(12) United States Patent
Kahl

(10) Patent No.: US 8,162,357 B2
(45) Date of Patent: Apr. 24, 2012

(54) MICROFLUID SYSTEM CONNECTION

(75) Inventor: Johan-Valentin Kahl, Munich (DE)

(73) Assignee: ibidi GmbH, Martinsried (DE)

( * ) Notice: Subject to any disclaimer, the term of this patent is extended or adjusted under 35 U.S.C. 154(b) by 0 days.

(21) Appl. No.: 10/506,028

(22) PCT Filed: Feb. 28, 2003

(86) PCT No.: PCT/EP03/02086
§ 371 (c)(1),
(2), (4) Date: Jan. 21, 2005

(87) PCT Pub. No.: WO03/072251
PCT Pub. Date: Sep. 4, 2003

(65) Prior Publication Data
US 2005/0118068 A1    Jun. 2, 2005

(30) Foreign Application Priority Data

| Feb. 28, 2002 | (EP) | 02004685 |
| Apr. 22, 2002 | (DE) | 102 17 846 |
| Aug. 21, 2002 | (DE) | 102 38 266 |

(51) Int. Cl.
*F16L 25/00* (2006.01)

(52) U.S. Cl. ............ 285/332.1; 285/332; 285/921

(58) Field of Classification Search ........... 285/332, 285/332.1, 921; 604/905; 422/502–508
See application file for complete search history.

(56) References Cited

U.S. PATENT DOCUMENTS

| 2,048,852 A * | 7/1936 | Dumas | 134/166 C |
| 3,640,552 A * | 2/1972 | Demler et al. | 285/110 |
| 3,871,770 A * | 3/1975 | von Behrens et al. | 356/343 |
| 3,888,523 A * | 6/1975 | Bartholomew | 285/382 |
| 4,555,050 A * | 11/1985 | Schiefer et al. | 222/597 |
| 4,819,684 A * | 4/1989 | Zaugg et al. | 137/112 |
| 4,895,500 A * | 1/1990 | Hok et al. | 417/566 |
| 4,991,883 A * | 2/1991 | Worden | 285/334.4 |
| 5,232,669 A * | 8/1993 | Pardinas | 422/100 |
| 5,312,377 A * | 5/1994 | Dalton | 604/534 |
| 5,343,909 A * | 9/1994 | Goodman | 141/242 |
| 5,890,745 A * | 4/1999 | Kovacs | 285/24 |
| 6,045,162 A * | 4/2000 | Haibara | 285/55 |
| 6,120,666 A * | 9/2000 | Jacobson et al. | 204/452 |
| 6,273,478 B1 * | 8/2001 | Benett et al. | 285/346 |
| 6,309,891 B1 * | 10/2001 | Shalon et al. | 436/180 |
| 2001/0019034 A1 * | 9/2001 | Tai et al. | 216/8 |
| 2001/0045235 A1 * | 11/2001 | Schick | 137/625.11 |
| 2002/0022809 A1 * | 2/2002 | Sudo et al. | 604/263 |
| 2002/0025256 A1 * | 2/2002 | Caren | 417/53 |
| 2002/0082586 A1 * | 6/2002 | Finley et al. | 604/535 |
| 2002/0086440 A1 * | 7/2002 | Lehtinen et al. | 436/180 |
| 2002/0117517 A1 * | 8/2002 | Unger et al. | 222/214 |

(Continued)

FOREIGN PATENT DOCUMENTS

WO    WO 98/10122 A1    3/1998

(Continued)

*Primary Examiner* — James Hewitt
*Assistant Examiner* — Jay R Ripley
(74) *Attorney, Agent, or Firm* — IP Strategies

(57) ABSTRACT

A microfluid system includes at least one flow-through volume, and at least one connector connected to the flow-through volume. The microfluid system includes a structured surface having at least one elevation. Each elevation is a tapered elevation. Each connector is formed in a respective elevation and is configured as a tapered recess.

25 Claims, 16 Drawing Sheets

U.S. PATENT DOCUMENTS

2002/0193754 A1* 12/2002 Cho .......................... 604/272

FOREIGN PATENT DOCUMENTS

| WO | WO 00/21659 | A1 | 4/2000 |
| WO | WO 01/30490 | A1 | 5/2001 |
| WO | WO 01/71331 | A1 | 9/2001 |
| WO | WO 02/30560 | A2 | 4/2002 |

* cited by examiner

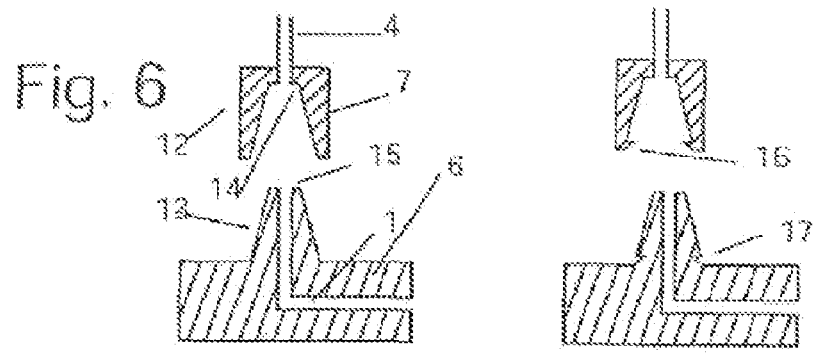
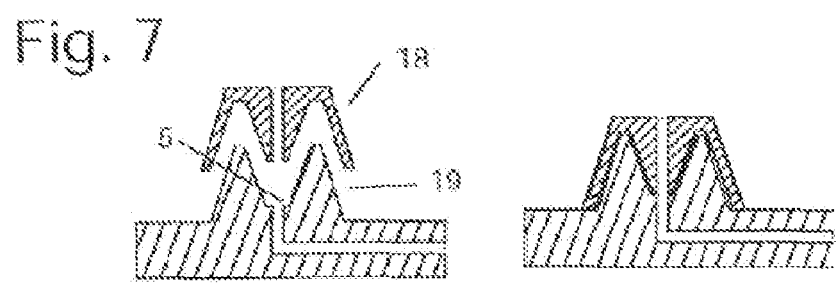
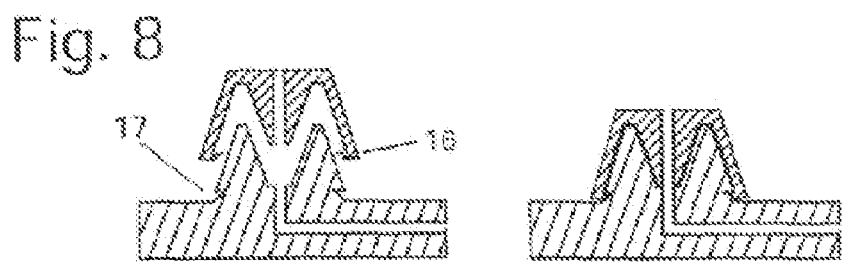

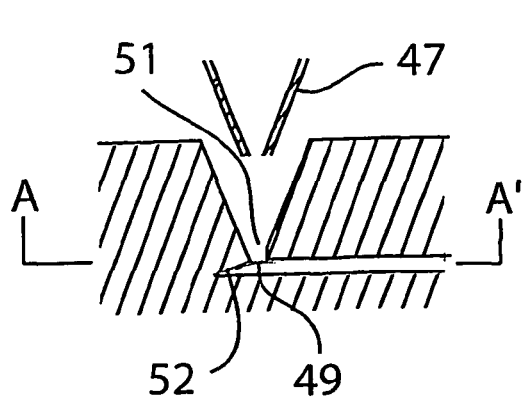
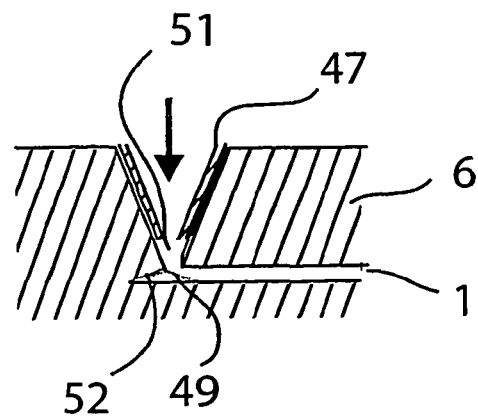
Fig. 20 a
Fig. 20 b
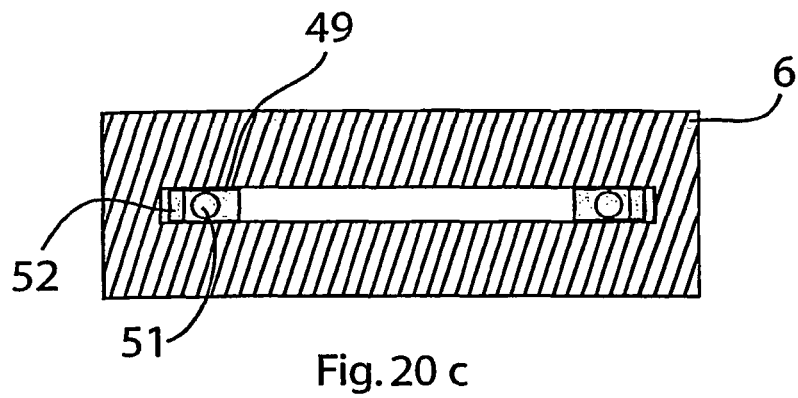
Fig. 20 c
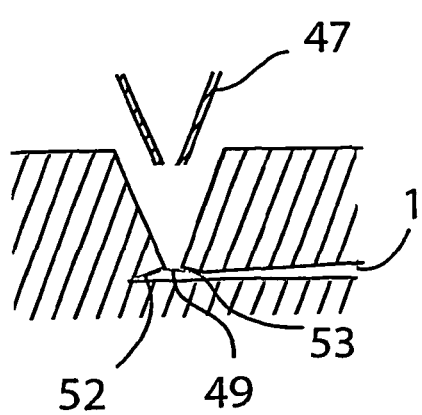
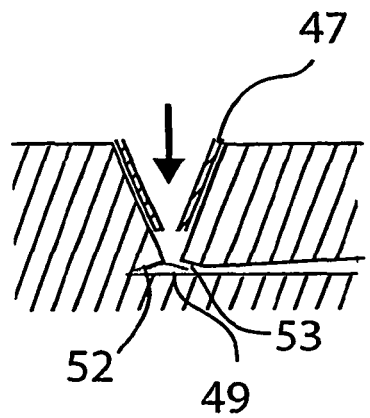
Fig. 21a
Fig. 21b

MICROFLUID SYSTEM CONNECTION

BACKGROUND OF THE INVENTION

The present invention relates to a microfluid system comprising at least one flow-through volume and at least one connection means connected to the volume, and to a plug means for use in such a microfluid system.

Microfluid or microfluidic systems show high potential in analysis and diagnostics in biological and medical applications. Moreover, they can be used for the synthesis of chemical and biological products, for example as flow reactors.

Microfluidic systems are characterized in that very small amounts of liquid media are transported in small structures. The liquid volume ranges here from 10 ml to less than 1 nl. A clear trend in microfluidics is that individual components are to be interconnected by special connections to obtain a whole system. Apart from the interconnection of microfluidic components, it is particularly the connection to the macroscopic world that poses a great challenge. Due to the miniaturized structural dimensions, which are normally between nanometers and millimeters, special demands are made on the connections.

These demands are: easy connection and disconnection of the connections; high stability with respect to unintended disconnection; high density with respect to gas and liquid exchange; small dead volumes in relation to the volume of the microfluidic components; preventing the penetration of undesired air when the connection is established (air bubbles), guaranteeing sterile conditions. Moreover, the connections should be biocompatible and possibly transparent to be able to check, for example, whether the medium actually flows through the structure. The solution should be parallelizable and advantageous in terms of production.

There exist numerous apparatuses designated as microfluidic systems.

U.S. Pat. No. 5,170,286 (WO 9215037) discloses, for instance, an observation chamber for microscopy in combination with a connected flow system. This is a "sandwich" construction that consists essentially of a special mounting ('central chamber element') into which microscopy cover glasses are inserted, the glasses being fixed by cover plates. Throughflow must be generated in this chamber through hose connections to a reservoir, which is not mounted on the chamber. No information is furnished about the connections, especially their properties such as stability, tightness, easy handling, dead volumes, etc. Nor is it described how this can be guaranteed with respect to the connection geometry.

WO 97/38300 describes a microchannel system of acryl that serves electrophoretic separation. The microchannel, however, is not used for flushing liquid therethrough. This document is also silent about the connection geometry with respect to the said demands.

WO 90/05295 also describes an optical biosensor system with channels. The liquid to be analyzed is passed on by means of valves and pumps. The document is also silent about any special geometry of the connections and special types of the connections for solving said problems.

DE 197 11 281 C21 also describes an apparatus with microfluid components. This patent specification places emphasis on the arrangement and integration of the functional layers in the carrier. It is in general silent about the geometry of the connections.

The said documents are silent about cover systems which close the flow chambers and contain special integrated components.

It is therefore not known from the prior art concerned with microfluid systems how the above-mentioned properties of connections and terminals are to be realized.

Although formerly existing connections for filling gases or liquids, e.g. hose clamps, efficiently prevent gases and liquids from exiting, they are very difficult to handle in a miniaturized form. The standardized connections known from medical engineering (Din-Taschenbuch 227, Medizinische Einmalartikel, Vertikale Normen Beuth Verlag 1999) have in general a dead volume that is much too large in relation to the total volume. As a consequence, it is above all impossible to handle small sample amounts. Moreover, the plug connections as shown there are not intended or optimized for use with microfluidic components, such as planar flow chambers. With many applications, the use of screw plugs contradicts the demand that a liquid should be adapted to be filled rapidly into a channel. These screw plugs, however, can and are used for tightly closing, for instance, flow chambers. Moreover, glued connections are not suited for analysis chips that can only be used once.

BRIEF SUMMARY OF THE INVENTION

It is the object of the present invention to overcome said drawbacks and to provide a microfluid system and a plug means which permit the throughflow and exchange of small liquid amounts in a rapid and easy way and/or the closing of small liquid volumes.

This object is achieved by a microfluid system according to claim 1 and by a plug means according to claim 7.

A microfluid system is here concerned comprising at least one flow-through volume and at least one connection means connected to the volume and configured in the form of a tapered recess or a tapered elevation. With this special geometry of the connection means it can be ensured that a plug means can be connected in a rapid, simple and particularly liquid-tight manner to the microfluid system. Moreover, the dead volume can be reduced by this geometry.

Another advantage of the microfluid system described therein is that the microfluid system itself can be made very thin in the form of a conventional object carrier (e.g. 1-1.5 mm thick) while external components that can be assembled and disassembled again can be used for the additional equipment needed, for instance for the liquid supply.

Preferably, the connection means is tapered conically, hyperbolically, conically in sections and/or hyperbolically in sections. This permits a firm connection of plug means. Particularly, plug means can be used with different shapes and dimensions, the plug means being adapted to be plugged to differently large extents into or onto the connection means, depending on the respective shape and/or dimension.

It is of advantage when the connection means is adapted in its shape and/or dimensions to laboratory components that are normally used. For instance, the tapered recess can be adapted to standard pipette sizes and shapes. With a recess that is conical in sections, the recess consists, so to speak, of successive truncated cones with different opening angles, preferably decreasing downwards. As a result, different pipettes with different inclination or opening angles can be firmly connected to the connection means. The dead volumes can thereby be reduced even further. Due to the special form of the recess, thin pipette tips with a small liquid volume can be inserted into the connection means more deeply than large pipette tips. The liquid or air volume between the pipette tip and the flow-through volume is thus minimized. Therefore, pipette tips of different sizes can be used for the same connection means, all of the pipette tips tightly terminating with the connection means.

With a hyperbolic recess, liquids can be pressed with the help of a pipette into the flow-through volume. As an alternative, the liquids will flow into the volume due to capillary and/or gravitational force when the pipette is removed.

A connection means in the form of a tapered elevation can be configured such that it is adapted to injection bottle stoppers and/or cap type bottle stoppers. The material of the injection bottle stoppers may e.g. include rubber or chlorobutyl.

According to an advantageous development of all of the previously described microfluid systems, the microfluid system has a structured surface. Preferably, the structure is in the form of elevations, particularly tapered elevations. It is of advantage when the connection means are formed in these elevations, particularly in the form of a tapered recess. The inner and outer shape and dimension of such an elevation with a connection means formed therein can be adapted to normally used laboratory components. This may have the effect that a plug means can be mounted in a rapid, simple and stable way due to the tapered elevation. At the same time, a firm and tight connection for the throughflow of liquids can be achieved through the adapted recess.

According to an advantageous development of all of the previously described microfluid systems, the connection means comprises a shoulder. As a consequence, a plug means can only be inserted up to the shoulder onto or into the connection means. Especially with a connection means in the form of a recess, it can thus be prevented that a plug means will clog the flow-through volume by being inserted too deeply. Such a shoulder need not surround the whole inner or outer circumference of the connection means; for instance, it may be configured in the form of a semi-ring.

Preferably, the connection means of the formerly described microfluid systems comprises a recess for receiving a snap-in element. Thus a plug means can be firmly connected to the connection means and rapidly disconnected again with a snap-in element. The recess may surround the whole connection means or may only be formed at individual places.

Preferably, the connection means of all of the previously described microfluid systems is designed as a connection means for receiving a Luer Lock element.

If the plug means need not be rapidly connected to and disconnected from the connection means, the connection means may comprise a thread. This will establish a particularly firm and stable connection between a plug means and the connection means.

According to an advantageous development of all of the previously described microfluid systems, a closing element is arranged on the connection means for closing the connection means. It is thereby e.g. possible to prevent impurities from penetrating if the connection means is not connected, for instance, to a plug. Such a closing element may either be designed such that it can be opened in a reversible manner or that it can only be opened in an irreversible manner. The closing element may e.g. be configured as a film or membrane. Such a closing element can then be opened in an irreversible manner in that upon application of pressure it is perforated by a plug, a pipette, a liquid, or the like. For a reversible opening possibility the closing element may be movably arranged so that e.g. when subjected to pressure it is moved from a position closing the connection means into a position in which the connection means is opened. Upon completion of such a pressure application the closing element can again be returned into the closing position.

A preferred closing element may have a functionalized or treated surface. The surface may e.g. be hydrophobic.

In a preferred development of all of the previously described microfluid systems, at least one further flow-through volume is formed in the microfluid system, the volume opening above the at least one flow-through volume into the connection means. It is thereby possible to close the at least one channel by a plug arranged on the connection means.

It is of advantage when the connection means of all of the above-described microfluid systems comprises an optically transparent material. It can thus be checked optically whether a liquid flows through the connection means and/or the volume, whether gas bubbles are formed and/or whether an optimum connection exists between the connection means and a plug means.

Preferably, the above-described microfluid systems comprise several connection means that are connected to one or several flow-through volumes. Particularly, the connection means may be arranged such that several connection means can be connected jointly to a plug device.

Advantageously, the material of all of the above-described microfluid systems comprises a glass of a high optical quality or a plastic material of a high optical quality, i.e. the plastic material has no birefringence and/or autofluorescence. Cyclic olefins and polycarbonate may here e.g. be used. Furthermore, the bottom and/or the top of the flow-through volume may have a thickness of less than 190 μm, depending on the demands of the analyzing methods used. Optimum properties are thus achieved for many analyzing methods.

For specific analyzing methods, such as interaction analyses between molecules, it is desirable to immobilize the molecules, macromolecules or cells. An inner surface of the flow-through volume and/or of the connection means may be surface-treated or functionalized for this purpose, for instance, by molecule groups, groups (such as —COO, —NH$_2$, ketones, alcohols) or macromolecules such as DNA or proteins. The samples immobilized on this surface may show a typical change in their spectrum upon reaction with a dissolved substance (e.g. molecule), or send a typical fluorescence signal. With the help of the microfluid system it is possible to flush out the dissolved molecules so that said signal can be analyzed quantitatively with low noise. In the area of the connection means, the inner surface of the microfluid system may be surface-treated or coated. This can e.g. be achieved in that the inner surface is hydrophobic in this area. A liquid can thus be passed away from the connection means into the flow-through volume, whereby e.g. impurities that are penetrating from the outside through the connection means can be kept away from the liquid.

The above-described microfluid systems may preferably be made of one piece. Hence, there are no elements that must be cleaned prior to use, and the system can be kept in a sterile condition with little efforts. Nor is it necessary to assemble the same in a complicated way prior to use. In such a case, it is normally intended for one-time use only.

According to the invention a plug means is also provided for use in one of the above-described microfluid systems, the plug means being configured such that it can be brought into engagement with the connection means.

This may particularly mean that the plug means is configured such that it can establish a firm, particularly liquid-tight, connection between the plug means and the connection means. To this end the plug means may comprise a tapered partial element that is adapted to the taper of the connection means. In the case of a connection means in the form of a tapered recess, the plug means may also comprise a partial element tapered in plugging direction or, in other words, downwards. By analogy, in a connection means in the form of a tapered elevation, the plug means may comprise a partial element tapered against the plugging direction. Hence, the connection between plug means and connection means may have a small dead volume.

In the case of a connection means in the form of a recess, the plug means may be configured such that it does not project beyond the surface of the microfluid system after it has been brought into engagement with the connection means.

According to a preferred development of all of the previously described plug means, said means is configured such that it abuts at least in part in planar form on the connection means and/or on part of the microfluid system surface that surrounds the connection means. This can lead to a particularly firm and stable connection to the connection means.

Advantageously, the above-described plug means are configured such that they can be brought into engagement with the connection means in a gas-permeable manner. This can be achieved in that there is at least in part a distance, e.g. by means of a spacer, between plug means and connection means. Plug means and connection means may be matched to each other such that the plug means can be brought into engagement in a gas-impermeable manner by being firmly pressed on. This can e.g. be achieved by spacers of an elastic plastic material in the form of bulges.

According to an advantageous development of all of the previously described plug means, said means comprise at least one snap-in element in the form of a bulge. The plug means can thus be brought into engagement with a corresponding connection means in a rapid way and establish a firm connection in addition. The plug means can then be configured in addition such that the snap-in elements can be easily disengaged again to disconnect the connection between connection means and plug means. To this end further bulges may be configured such that a torque is created by applying pressure, whereby the snap-in elements can be disengaged. All of the described bulges may surround the plug means or only be formed at individual places. The snap-in elements can e.g. be designed in the form of barbs.

According to an advantageous alternative the plug means comprises a thread. This permits a firm connection of plug means and connection means.

According to a further advantageous alternative the plug means may be connected in the manner of a crown cap to the connection means. The plug means is here pressed onto the connection means. Increased sterility can thereby be guaranteed.

Preferably, each of the described plug means may be designed such that it rests on part of the microfluid system surface surrounding the receiving means. This can ensure a stable connection between plug means and connection means.

According to a preferred development each of the previously described plug means comprises an optically transparent material. For instance, the throughflow through the plug means and/or the volume, the presence of air bubbles and/or the connection between plug means and connection means can thereby be checked optically.

It is of advantage when the previously described plug means comprise a biocompatible material. Undesired interaction between liquid and material can thus be avoided. The plug means may e.g. consist fully or in part of biocompatible material or may be coated fully or in part with a biocompatible material.

According to an advantageous development of all of the previously described plug means, said means comprise at least one through hole. A through hole permits the supply of liquid and/or gases.

Preferably, each through hole is connected to a supply means, particularly a hose. Each supply means may e.g. be connected to a liquid or gas source.

In an advantageous alternative, each through hole is configured such that it is adapted to the shape of normally used laboratory components (such as a pipette).

Advantageously, each through hole may be closed with a septum. The septa may e.g. be silicone, Teflon, natural rubber, rubber styrene-butadiene rubber or butyl. The material of the plug means may comprise plastics or aluminum.

Preferably, the described through holes comprise microfilters.

According to an advantageous development of the described plug means, these comprise closing elements. According to an advantageous alternative, the plug means is configured as a closing means on the whole. According to a further advantageous alternative, the closing element is configured like in the case of the previously described plug means. Particularly, the closing element may be designed as a film or membrane that is removed prior to use of the plug means.

It is of advantage when the previously described plug means comprise electronic components, liquid reservoirs and/or gas reservoirs. For instance, the plug means may comprise electrodes that are configured such that they extend into the flow-through volume, whereby an electric voltage can be applied in the liquid. They may also extend at the same time into a liquid reservoir integrated into the plug means and thus form a conducting connection between the liquid reservoir and the flow-through volume. The electronic components may additionally be designed as control means and control the addition of liquid and/or gas into the flow-through volume. Alternatively, this addition can also be controlled via external connections. The control operation may e.g. regard the amount and/or duration; the adding operation may take place by means of compressed air. A further advantage of this development is that the required amount of liquid or gas can be strongly reduced through the immediate vicinity of the liquid or gas reservoir. Advantageously, the integrated liquid reservoirs may comprise a through hole that opens above the base surface into the liquid reservoir. Hence, when a liquid flows out of the flow-through volume through the through hole into the liquid reservoir, a backflow is prevented.

The invention also provides a plug device consisting of at least two plug means that are configured as a unit. Such a plug device can be brought into engagement with a plurality of connection means at the same time.

If the plug device comprises at least two liquid reservoirs, these may advantageously be interconnected via a passage opening. Microfilters may e.g. be arranged in said passage opening.

With connection means formed as tapered recesses, the plug device and the connection means may also be configured such that the plug device does not project beyond the surface of the microfluid system after it has been brought into engagement with the connection means.

A plug-type module is provided by the plug device that may e.g. comprise a reaction, collection and/or purification area.

Moreover, the invention provides a system that comprises at least one of the previously described microfluid systems and at least one of the previously described plug means and/or devices.

Moreover, the invention provides a microfluid system having at least one flow-through volume, wherein each flow-through volume opens into a liquid reservoir and the opening of each volume is arranged above the base surface of the corresponding liquid reservoir. The microfluid system can particularly be one of the above-described microfluid systems.

Such a microfluid system has the advantageous effect that a liquid flowing through the flow-through volume into the liquid reservoir is received by the liquid reservoir and no longer flows back into the flow-through volume. For instance, the volume can thus be flushed with different liquids in direct succession, each of the liquids being then received by the liquid reservoir so that the liquids do not intermix in the volume.

According to an advantageous development of said microfluid system, each liquid reservoir may be arranged on the surface of the microfluid system. Each reservoir is thus accessible easily and rapidly from the outside, which e.g. facilitates the removal of liquid from the reservoir. Each reservoir may be covered.

Preferably, each flow-through volume may be guided through a hollow cylinder configured within the corresponding liquid reservoir to stand on the base surface of the liquid reservoir. Hence, the flow-through volume is passed through the base surface of the liquid reservoir. The cross section of the hollow cylinder may be designed in any desired manner; for instance, it may be a hollow cylinder with a circular cross-section on the inside and outside. The microfluid system can thus be produced easily. Each hollow cylinder may be arranged directly along a side surface of the liquid reservoir and pass into the side wall or be arranged remote therefrom.

According to an advantageous alternative, the liquid reservoir comprises a side wall into which the flow-through volume is integrated in part. The opening of the volume is thus positioned in the side wall above the base surface of the reservoir.

Each flow-through volume may be passed through any other hollow body inside the liquid reservoir instead of a hollow cylinder. Such a hollow body may e.g. be tapered in one direction.

When each flow-through volume inside the liquid reservoir is designed as a hollow cylinder, the hollow cylinder may have a beveled surface. This prevents exiting liquid from splashing upwards; instead of this, it will flow to the side.

Preferably, the material of the microfluid system may be a plastic material such as polycarbonate or polyolefins, resulting in an easy manufacture by means of injection molding methods or extrusion.

BRIEF DESCRIPTION OF THE DRAWINGS

Further features of the invention will now be described with reference to the embodiments in the drawings, which schematically show in:

FIG. 6 a cross section through a connection means in the form of a conical elevation and with a plug means with and without a snap-in element;

FIG. 7 a cross section through a microfluid system with a structured surface and a connection means in the form of a conical recess;

FIG. 8 a cross section through a microfluid system with a structured surface and a plug means with a snap-in element;

FIGS. 20a, 20b and 20c a cross section through a further microfluid system with a closing element;

FIGS. 21a 21b a variant of the microfluid system of FIGS. 19a and 19b;

DETAILED DESCRIPTION OF THE INVENTION

Figure 1:
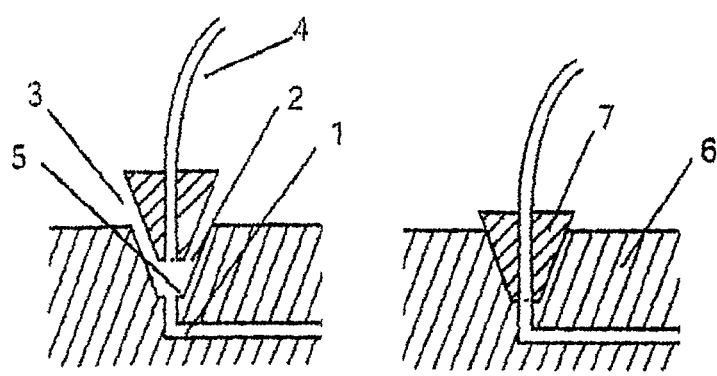
FIG. 1 a cross section through a microfluid system of the invention and a plug means in the form of a recess.

FIG. 1 shows the cross section of a microfluid system 6 and a plug means 7. Inside the microfluid system 6, there is a flow-through volume 1 in combination with the connection means in the form of a recess with a conical taper 2 and a shoulder 5 to avoid dead volumes. The plug means is also configured in the form of a conical taper 3 in plugging direction. The plug means comprises a through hole to which a hose or flexible tube 4 is connected.

Figure 2:
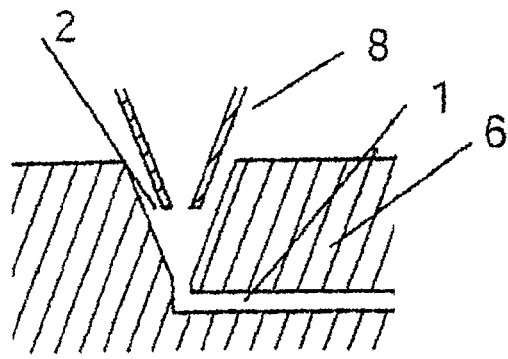
FIG. 2 a cross section through a microfluid system comprising a connection means adapted to a pipette tip.

FIG. 2 shows the cross section of a connection means, which is optimized for a pipette tip 8. Thus liquid can be filled with a pipette into the volume 2 of the microfluid system 6 with the conical bevel 2 without any dead zones. As for commercial pipettes, the minimum (lower) inner diameter may be between 0.4 mm and 1 mm, the maximum (upper) inner diameter between 0.7 mm and 6 mm, and the depth of the recess between 1 mm and 15 mm.

Figure 3:
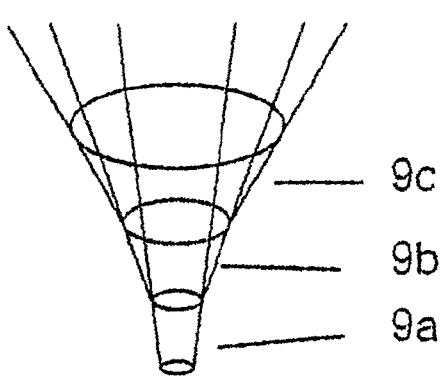
FIG. 3 a three-dimensional view of the shape of a connection means in the form of a recess with a taper that is conical in sections.

FIG. 3 shows the shape of a connection means in the form of a recess with a taper 9a, 9b and 9c which is conical in sections, wherein the opening angle of the truncated cones decreases downwards, in a three-dimensional view. Different pipette tips can thus be used without the formation of a significant dead volume.

Figure 4:
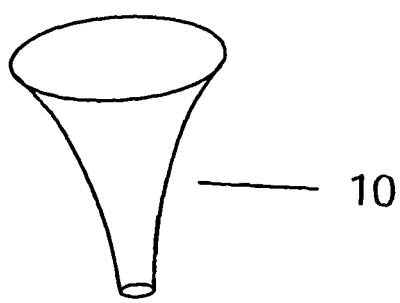
FIG. 4 a three-dimensional view of the shape of a connection means in the form of a recess with a hyperbolic taper.

FIG. 4 shows the shape of a connection means in the form of a recess with a hyperbolic taper 10.

Figure 5:
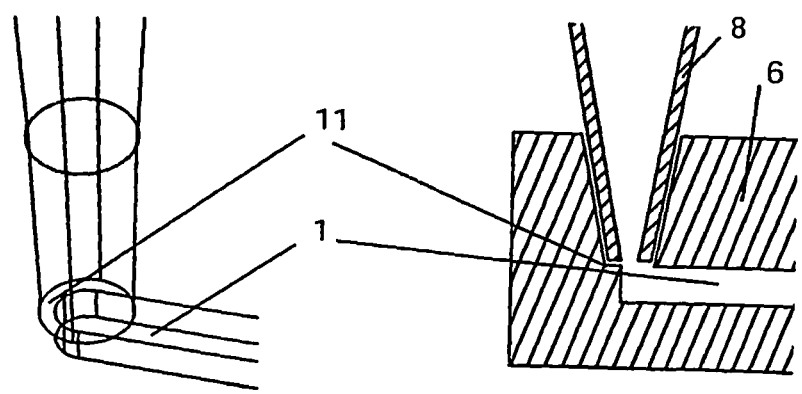
FIG. 5 a three-dimensional and cross-sectional view illustrating a connection means with a shoulder.

FIG. 5 is a three-dimensional and cross-sectional view illustrating an embodiment of a microfluid system 6 with a connection means having a shoulder 11. It is thereby ensured that the liquid inside the pipette tip 8 can also pass into the flow-through volume 1 when the pipette tip is fixedly mounted. The shoulder is here configured in the form of a semi-ring.

FIG. 6 shows two embodiments of a connection means in the form of a conically tapered elevation 13. The plug means 7 which is adapted to the connection means is provided on the inside with a conical taper towards the plug means. The outer surface 12 is cylindrical. To avoid dead volumes, shoulders 14 and 15 are formed on the plug means and on the connection means. In contrast to the embodiment at the left side, the example at the right side shows snap-in elements 16 in the form of barbs and corresponding recesses 17. As a result, the plug means can be connected particularly firmly and tightly to the connection means.

The connection means may e.g. be designed in the form of a conical elevation, wherein the opening angle of the truncated cone is 60° and the minimum (upper) diameter is between 3.5 mm and 4.5 mm. The height of the elevation may vary between 6 mm and 9 mm. The Luer connectors known in the medical field can thus be connected in an advantageously firm manner to the microfluid system.

FIG. 7 shows an embodiment of a microfluid system with a structured surface in the form of a conical elevation 19. The connection means is designed in the form of a conically tapered recess. As a result, both the outer and the inner dimensions can be adapted to the dimensions of standard laboratory components. For instance, standard plugs, pipette tips and also special plugs can be used. In the illustrated example the plug means is configured such that it covers part of the surface surrounding the connection means, whereby stability is increased. Like in FIG. 1, a shoulder 5 is here shown for avoiding dead volumes. At the right side the connection means and the microfluid system are shown in the connected state.

FIG. 8 shows a similar microfluid system with plug means as in FIG. 7. However, barbs 16 are provided on the plug means and recesses 17 on the connection means, the recesses permitting a particularly firm and tight mounting of the plug means on the connection means.

Figure 9A:
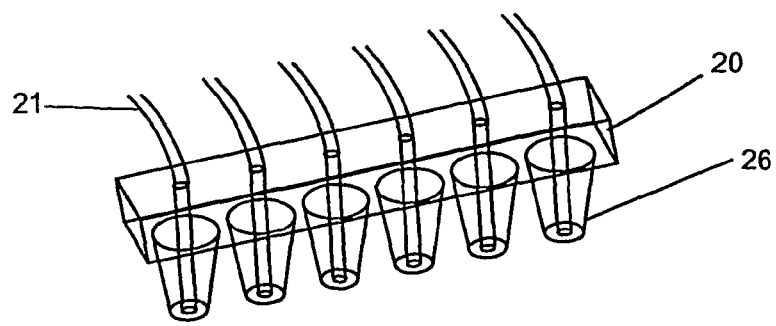
FIG. 9a a perspective view of a plug device.

FIG. 9a shows a plug device where a plurality of plugs are configured as a unit. The plug device comprises a plug strip 20 on which conically shaped partial elements 26 are arranged. Flexible tubes 21 are connected to the plug strip.

Figure 9B:
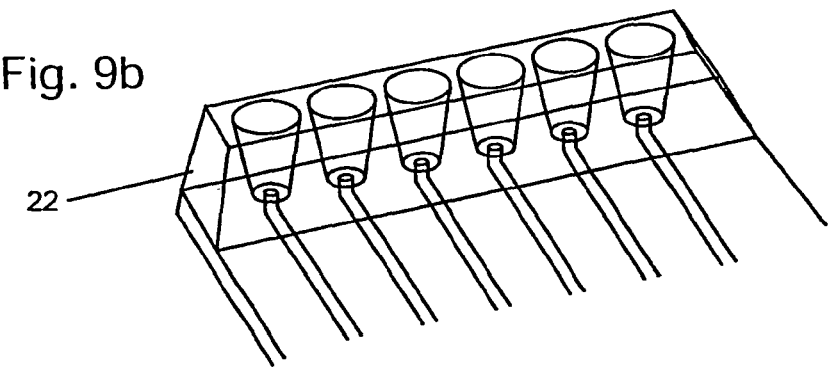
FIG. 9b a perspective view of a microfluid system with a connection device.

FIG. 9b shows a microfluid system corresponding to the plug device of FIG. 9a and comprising a connection device 22 that includes a plurality of connection means and flow-through volumes connected thereto.

Figure 9C:
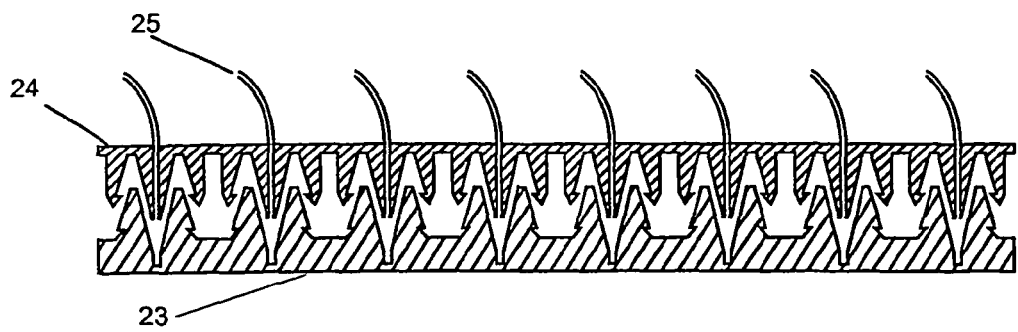
FIG. 9c a cross section through a system consisting of a plug device and a microfluid system with a connection device.

FIG. 9c is a cross section through a plug device 24 with flexible tubes 25 and a connection device 23. The connection device 23 can be firmly connected to the plug device 24 via corresponding barbs.

Figure 10A:
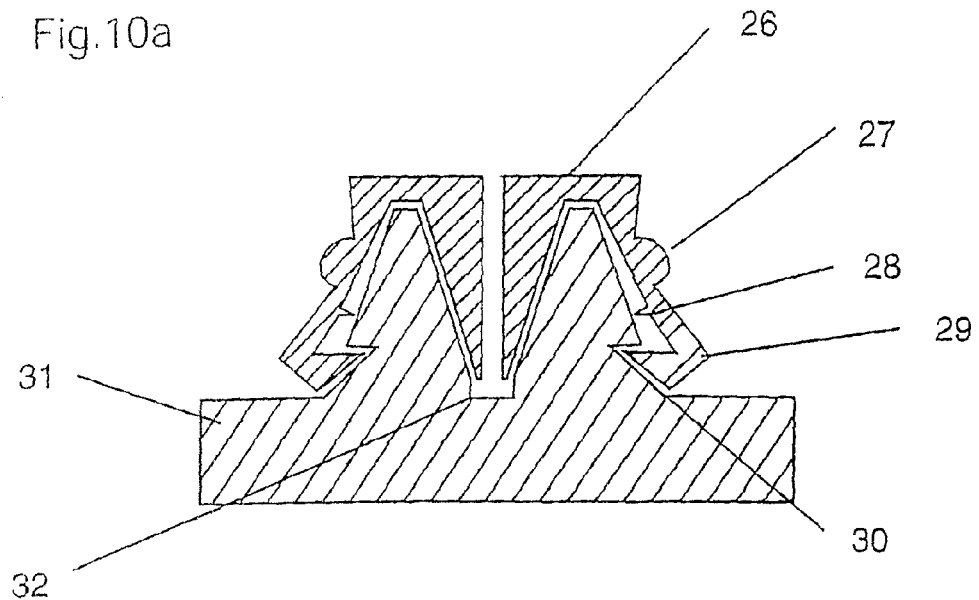
FIG. 10a a cross section through a microfluid system and a plug means with bulges for disconnecting the plug means.
Figure 10B:
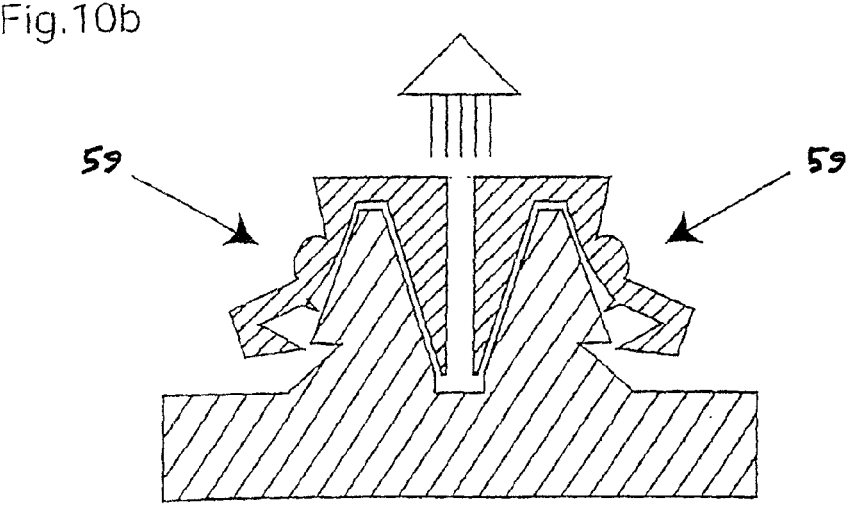
FIG. 10b a cross section through a microfluid system and a plug means with disengaged snap-in elements.

FIG. 10a shows an embodiment of a barb system as a cross-sectional drawing. An additional bulge 27 and a spacer 28 are provided in the plug means 26. With the barb 29, the plug means is firmly connected to the microfluid system 31 through the recess 30, so that the volume 32 can be filled easily. On account of the spacer 28 a torque is generated by compressing 59 the bulges 27 (see FIG. 10b), the torque moving the barbs 29 apart and thereby disconnecting the plug means from the connection means.

Figure 11:
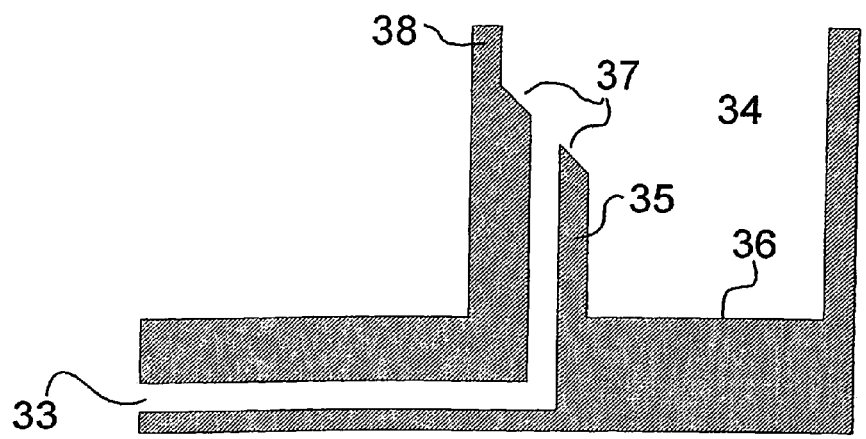
FIG. 11 a cross section through a microfluid system comprising a flow through volume and a liquid reservoir.

FIG. 11 shows a microfluid system with a flow-through volume 33 which opens into a liquid reservoir 34. A hollow cylinder standing on the base surface 36 is formed inside the reservoir 34. The flow-through volume 33 is guided through the base surface 35 through the hollow cylinder 35. The hollow cylinder 35 is arranged directly along a side wall 38 and passes thereinto. The surface 37 of the cylinder 35 is beveled at the opening side.

Figure 12:
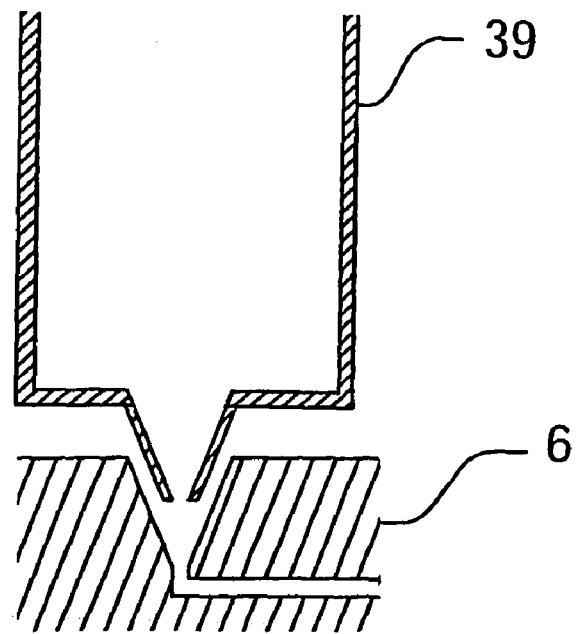
FIG. 12 a cross section through a microfluid system and a plug means with a liquid reservoir.

FIG. 12 shows an embodiment of a plug means 39 comprising a liquid reservoir. The connection means is configured to receive a Luer-Lock element.

Figure 13:
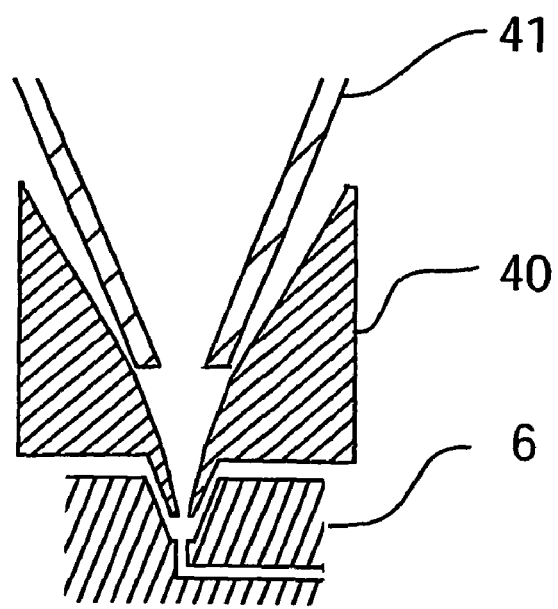
FIG. 13 a cross section through a microfluid system and a plug means with a through hole for a pipette.

FIG. 13 shows an embodiment of a plug means 40 which comprises a through hole for receiving a pipette or syringe tip 41. Hence, in this case, the plug means assumes the function of an adapter.

Figure 14:
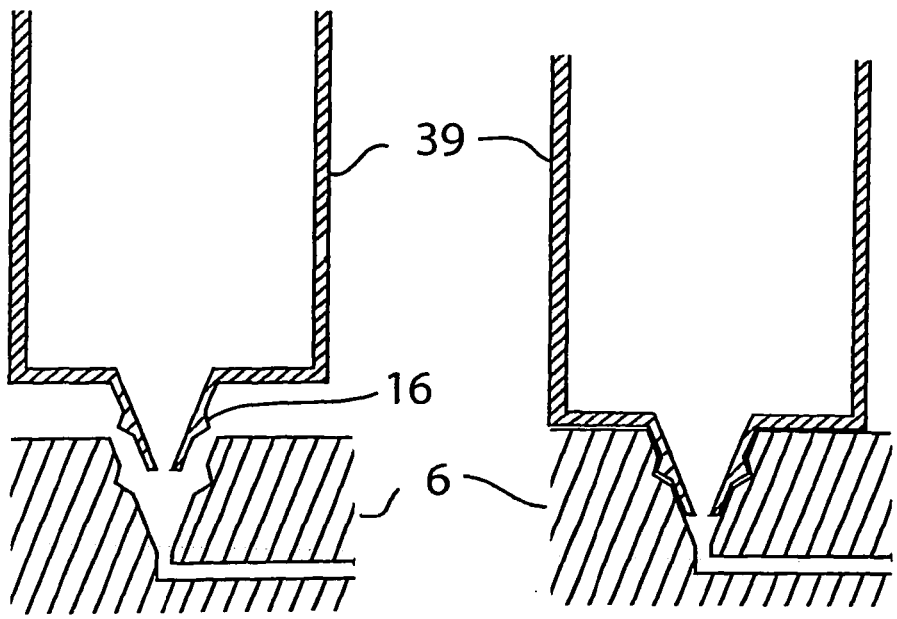
FIGS. 14a and 14b a cross section of a further example of a microfluid system and a plug means with a liquid reservoir.

FIG. 14a shows a microfluid system 6 and a plug means 39 with a liquid reservoir, the plug means 39 comprising snap-in elements 16. FIG. 14b shows the plug means in the plugged state.

Figure 15:
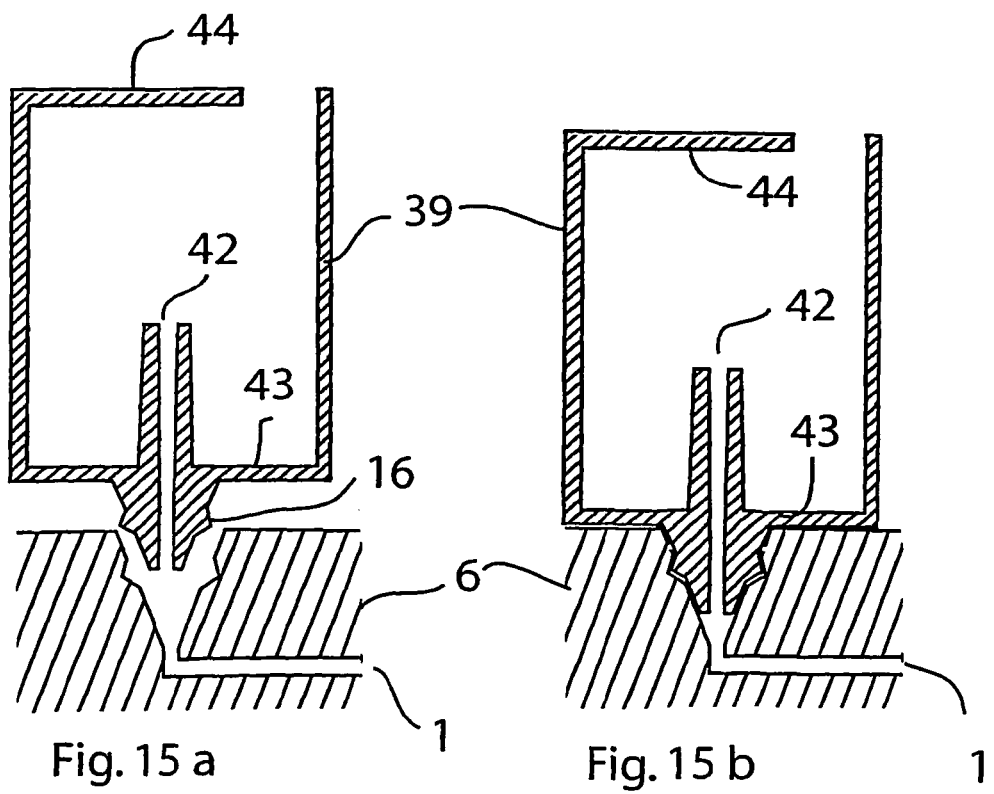
FIGS. 15a and 15b a cross section of a further example of a microfluid system and a plug means with a liquid reservoir.

A further embodiment of a microfluid system 6 and a plug means 39 with a liquid reservoir is shown in FIGS. 15a and 15b. In this example the through hole 42 opens above the base surface 43 into the liquid reservoir. Hence, the liquid provided inside the liquid reservoir is prevented from flowing back into the flow-through volume 1. Thus, the liquid can be removed from the microfluid system and then be used further or disposed off. The liquid reservoir can be covered with a cover 44 at least in part.

Figure 16:
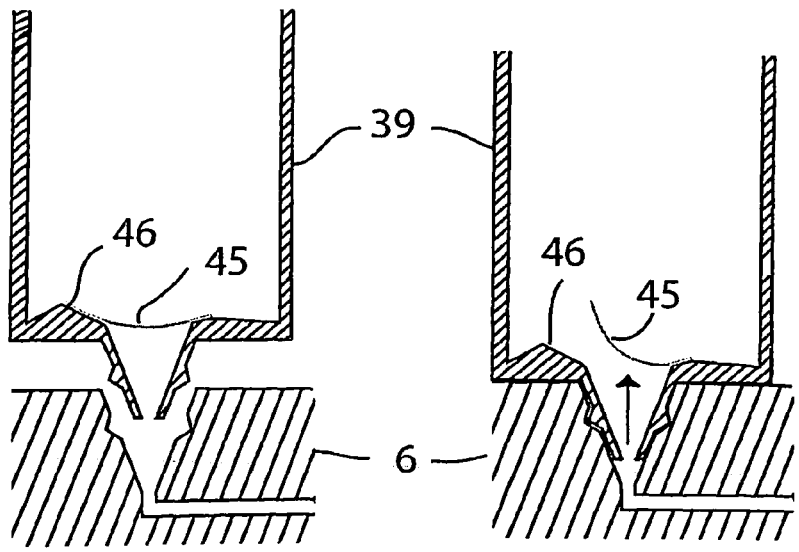
FIGS. 16a and 16b a cross section of a microfluid system and a plug means with a closing element.

FIGS. 16a and 16b show a microfluid system 6 and a plug means 39, wherein the through hole comprises a closing element 45 in the form of a film. The film is fixed at a place (here at the right side of the through hole) and has a curvature on account of which it closes the through hole by spring tension. Otherwise, the film is positioned around the through hole, preferably in a beveled area 46 to ensure an optimum closure through an enlarged support surface. When the film is acted upon by pressure (applied by a liquid or gas) from below through the through hole, as outlined in FIG. 16b with the arrow, a force acts against the spring force, so that the through hole is opened.

FIGS. 17a and 17b show a microfluid system with a flow-through volume 48 which opens above the first flow-through volume 1 into the connection means. When a plug means 47 is plugged into the connection means, it will thus close the flow-through volume 48; a liquid or a gas can then only pass into volume 1.

In FIGS. 18a and 18b, a closing element 49 is arranged in the connection means in the form of a curved film which due to its spring tension closes the connection means. A plug means plugged into the connection means presses the spring means to the side (FIG. 18b), so that the connection means is opened.

Figure 19:
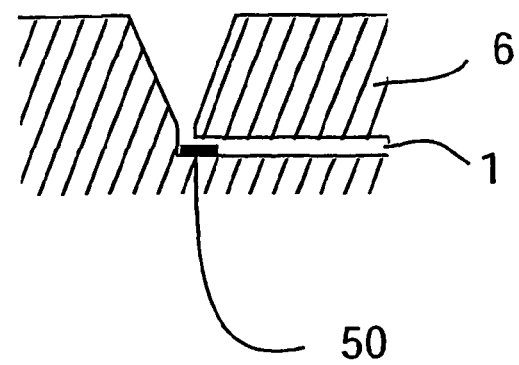
FIG. 19 a cross section through a microfluid system with a coated area.

FIG. 19 shows a microfluid system with a coated area 50 by which the inner surface of the flow-through volume 1 is hydrophobized underneath the connection means.

In FIG. 20a, a microfluid system 6 is seen with a closing element 49 in the form of a film that closes the opening 51 of the flow-through volume 1 into the connection means by spring force. The film is fixed in the area 52 to the inner surface of the volume 1. When the film is acted upon by pressure (as outlined by the arrow in FIG. 20b), the film is pressed downwards, thereby releasing the opening 51. FIG. 20c shows a cross section taken along axis A-A'.

FIGS. 21a and 21b show a variant of the microfluid system of FIGS. 19a and 19b, wherein the inner surface of the flow-through volume 1 is beveled in an area 53 of the opening to allow for an optimum closure through a larger support surface of the film 49.

Figure 22:
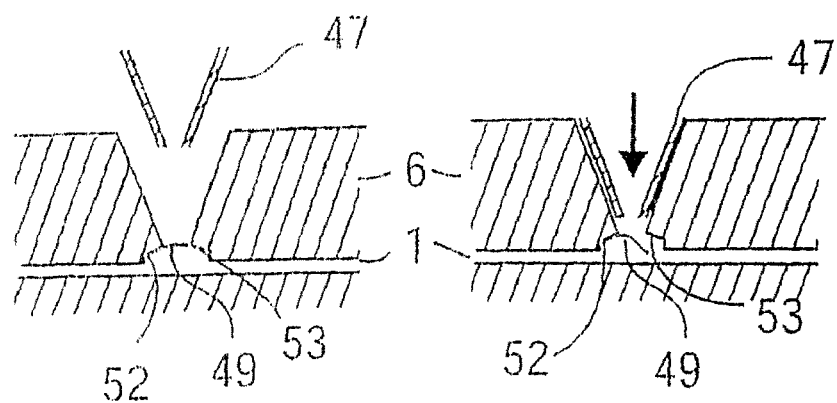
FIGS. 22a, 22b, 22c and 22d a cross section through a further microfluid system with a closing element.
Figure 22:
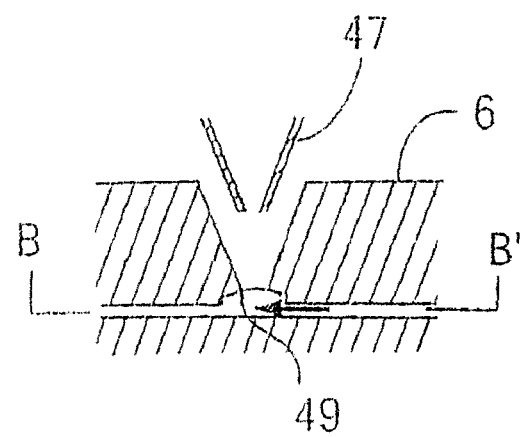
Figure 22:
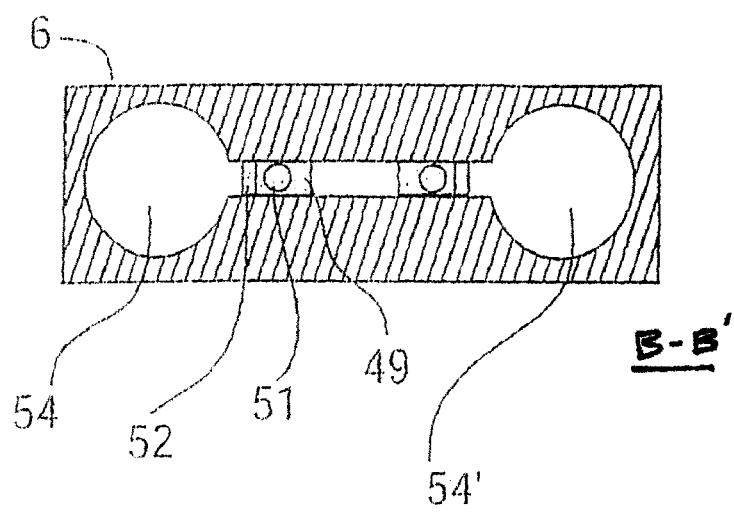

FIGS. 22a to 22d show a microfluid system 6 with a flow-through volume 1 which connects two reservoirs 54 and 54'. Two connection means which are closed by films 49 and 49' open into the channel. FIG. 22d is a cross section taken along axis B-B' of FIG. 22c. When a film is acted upon by pressure (FIG. 22b), it will open opening 51, but only one side of the volume 1 will become accessible. After the plug means 47 has been removed, the opening is again closed and the connection through the volume 1 to the other reservoir is released.

Figure 17:
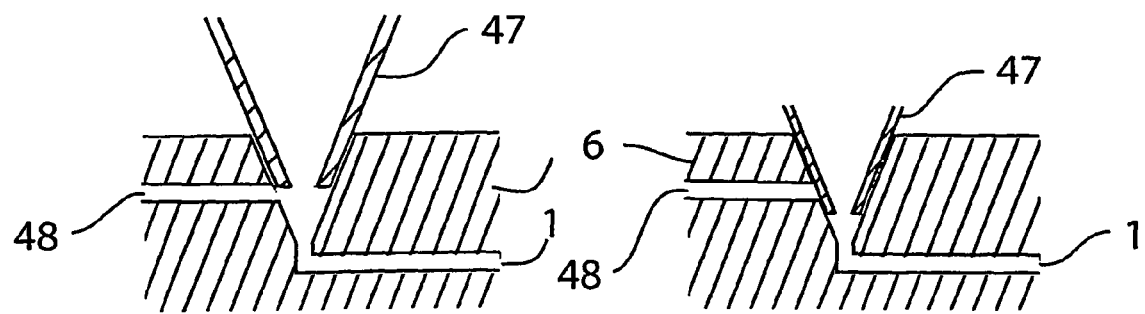
FIGS. 17a and 17b a cross section through a microfluid system with a flow-through volume closed by a plug means.
Figure 18:
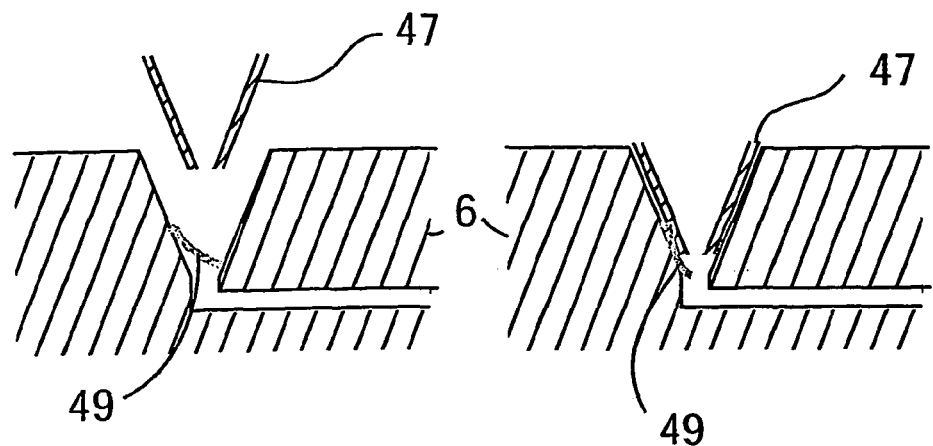
FIGS. 18a and 18b a cross section through a microfluid system with a closing element.
Figure 23:
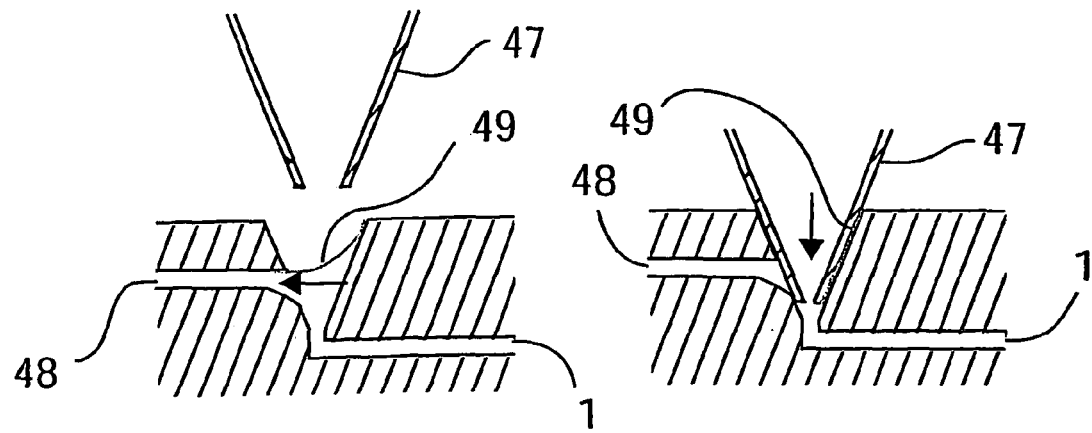
FIGS. 23a and 23b a cross section through a further microfluid system with a closing element.

FIGS. 23a and 23b show a combination of the embodiments of FIGS. 17 and 18. Without a plug means 47, the connection means is closed by a film 49 while channels 1 and 48 are in communication. If a plug means 47 is inserted into the connection means, the channel 48 will be closed thereby and the film 49 will be pressed to the side.

Figure 24:
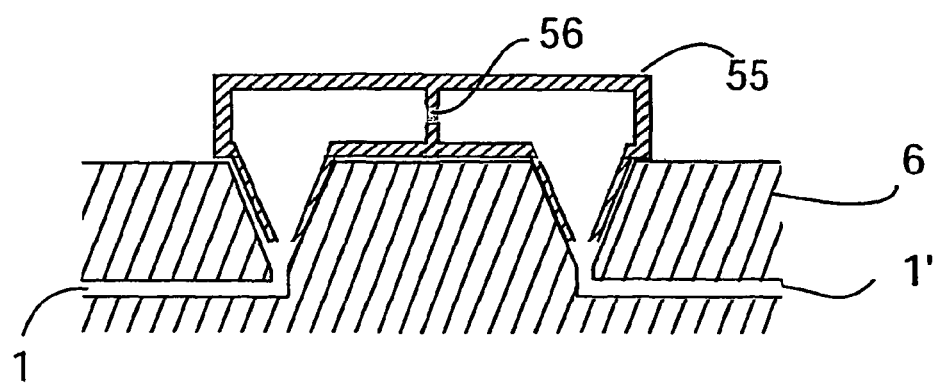
FIG. 24 a cross section through a microfluid system with a plug device.

FIG. 24 shows a microfluid system 6 comprising a plug device 55 which includes two liquid reservoirs that are again connected via a through hole 56 with microfilter.

Figure 25:
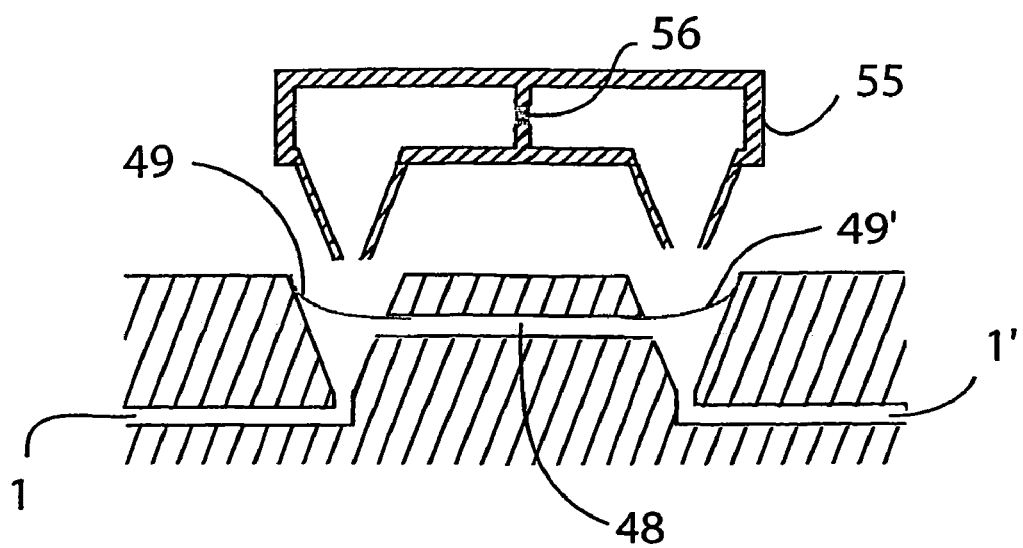
FIGS. 25a and 25b a cross section through a microfluid system with closing elements and a plug device.
Figure 25:
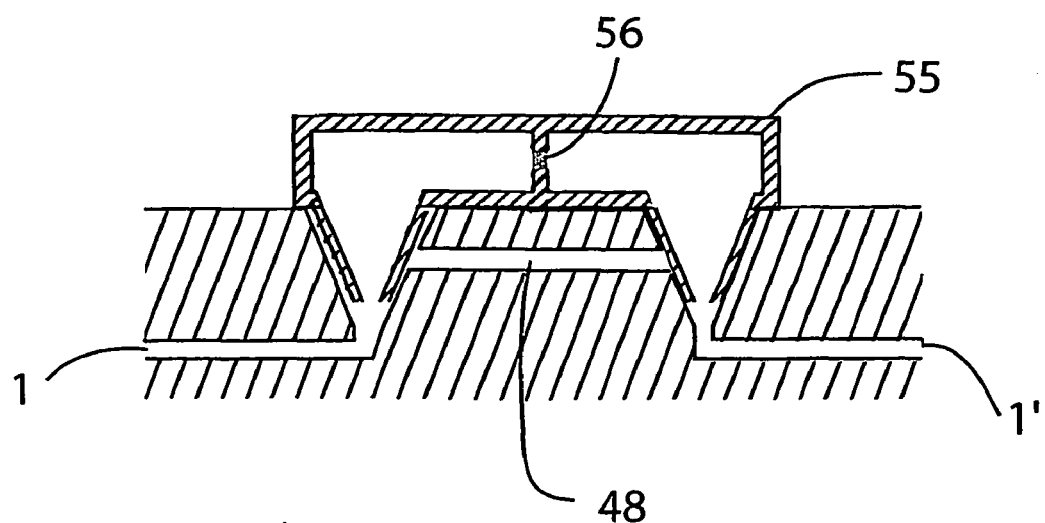

FIG. 25a shows a microfluid system comprising two connection means and an associated plug device. The connection means are interconnected via a channel 48 and closed to the outside via films 49 and 49'. When the plug device 55 is plugged (FIG. 25b), the channels 1 and 1' are only interconnected via the through hole 56 between the liquid reservoirs. Hence, the liquid can be filtered by a microfilter arranged in the through hole 56. Alternatively, the liquid reservoirs may e.g. serve as reaction areas which are again removed from the microfluid system after the reaction has taken place.

Figure 26:
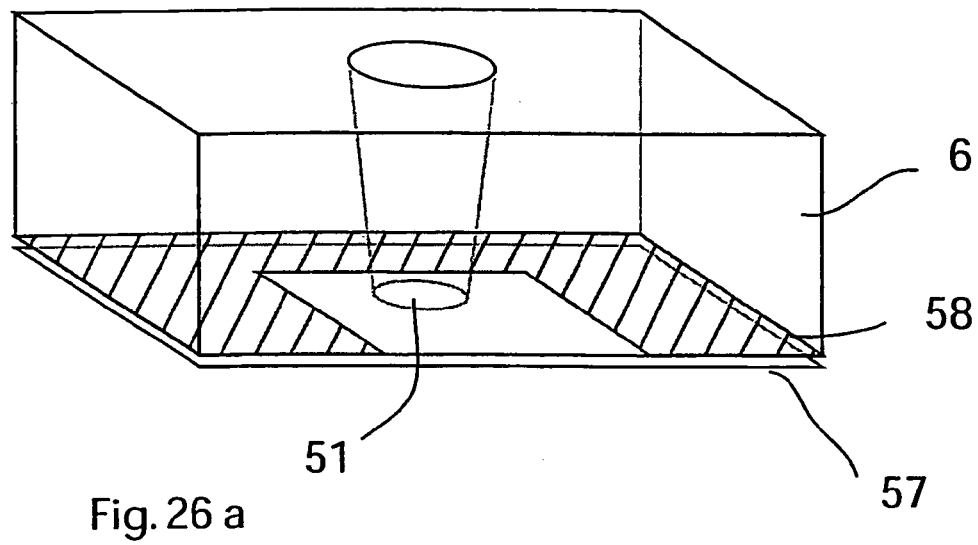
FIGS. 26a and 26b an exploded view of a microfluid system with a closing element.
Figure 26:
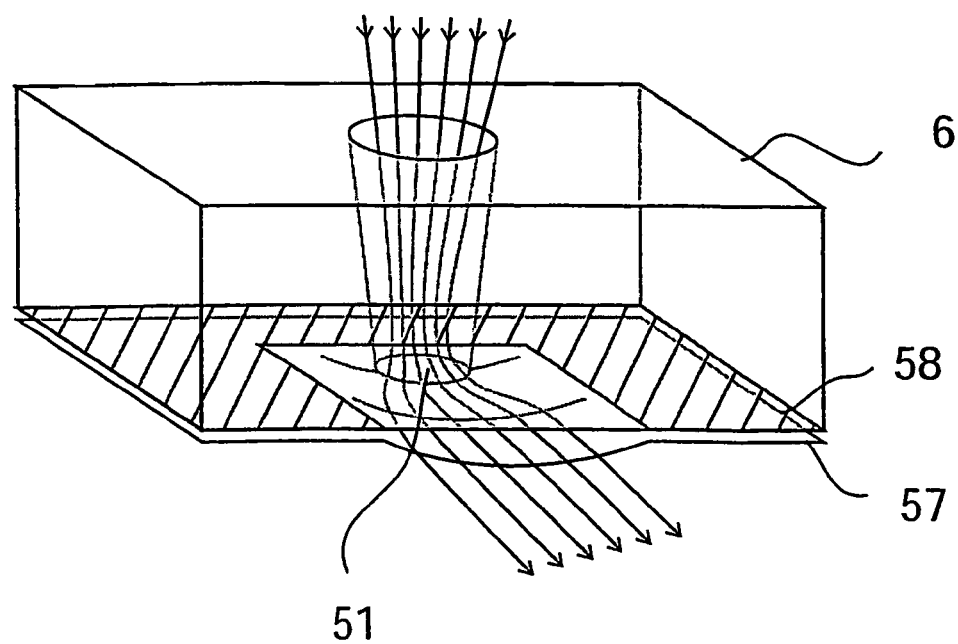

FIG. 26a shows an exploded view of a part of a microfluid system 6 with a closing element 57 in the form of an elastic membrane or film 57 that is directly arranged on the inner surface 58 of a flow-through volume and closes the opening 51 of the connection means. When acted upon by pressure (as illustrated in FIG. 26b by arrows), the membrane 57 will expand and release the opening 51.

Figure 27:
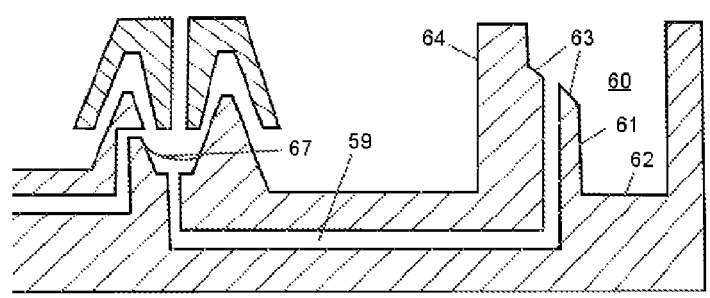
FIG. 27 a microfluid system with a closing element adapted to be arranged on the first connector, with an additional flow-through channel that opens into the recess above the first flow-through channel.
Figure 28:
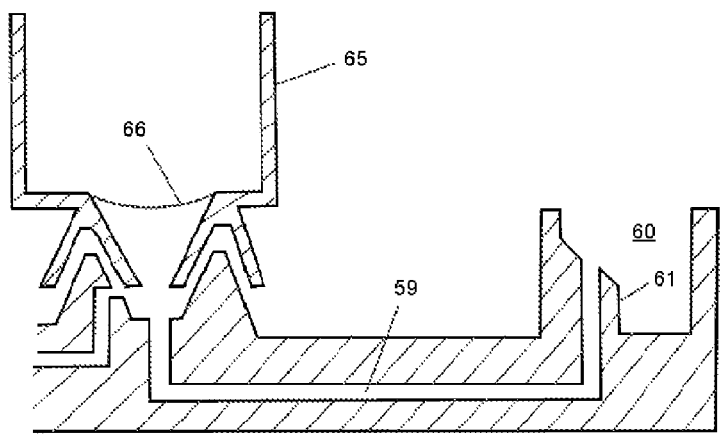
FIG. 28 a view of a microfluid system with a plug having a closing element.

In FIG. 27, a closing element 67 is arranged in the connection means in the form of a curved film which due to its spring tension closes the connection means. FIGS. 27 and 28 show the microfluid system having a flow-through channel 59 that opens into a liquid reservoir 60 above the channel. A hollow cylinder standing on the base surface 62 is formed inside the reservoir 60. The flow-through volume 59 is guided through the base surface to the hollow cylinder 61. The hollow cylinder 61 is arranged directly along a side wall 64 and passes thereinto. The surface 63 of the cylinder 61 is beveled at the opening side. FIG. 28 also shows a microfluid system and a plug means 65, wherein the through hole comprises a closing element 66 in the form of a film, as previously described.

It goes without saying that the features indicated in the above-described embodiments are not limited to these special combinations and are also possible in any other desired combinations.

The invention claimed is:

1. A microfluid system, comprising:
a base having at least a first flow-through channel; and
at least a first connector in fluid communication with the first flow-through channel;
wherein the base includes a surface and at least a first projection on the surface;
wherein an outer surface of the first projection has a conical taper from a proximate end disposed on the surface of the base to a narrower distal end elevated from the surface of the base to allow connection to a plug having a complementary surface; and
wherein the first connector includes a recess within the first projection that is tapered from a first opening at the distal end of the first projection to a narrower second opening into the first flow-through channel.

2. The microfluid system according to claim 1, wherein the recess is tapered according to at least one shape selected from the group consisting of conical, hyperbolic, conical in sections, and hyperbolic in sections.

3. The microfluid system according to claim 1, wherein the first connector includes a shoulder at the second opening of the recess.

4. The microfluid system according to claim 1, wherein the outer surface of the first projection includes a notch adapted to receive a snap-in element.

5. The microfluid system according to claim 1, further comprising a closing element adapted to be arranged on the first connector in order to close access to the first connector.

6. The microfluid system according to claim 1, further comprising a plug having a second flow-through channel;
wherein the plug includes a tapered portion in which the second flow-through channel is disposed, wherein a shape of the tapered portion corresponds to a shape of the recess of the first projection; and
wherein the plug is adapted to be removably coupled to the base when the tapered portion of the plug is inserted into the recess of the first projection, such that the first flow-through channel is in fluid communication with the second flow-through channel.

7. The microfluid system according to claim 1, wherein at least a portion of the first flow-through channel is substantially parallel to the surface of the base.

8. The microfluid system according to claim 1, wherein a first portion of the first flow-through channel adjacent the second opening of the recess is substantially perpendicular to the surface of the base, and a second portion of the first flow-through channel is substantially parallel to the surface of the base.

9. The microfluid system according to claim 1, wherein the base has a thickness in a range of 1 mm-1.5 mm.

10. A plug in combination with a microfluid system according to claim 1, wherein the plug is adapted to engage the first connector and comprises a first element tapered to correspond with the taper of the recess and a second element tapered to correspond to the taper of the first projection.

11. The plug in combination with the microfluid system according to claim 10, wherein the plug includes at least one surface adapted to engage the first connector such that the at least one surface of the plug engages at least one surface of the first connector in planar form.

12. The plug in combination with the microfluid system according to claim 10, wherein the plug includes at least one snap-in element in the form of a bulge.

13. The plug in combination with the microfluid system according to claim 10, wherein the plug includes at least one surface adapted to engage the first connector such that the at least one surface of the plug engages at least a portion of the surface of the base around the first projection in planar form.

14. The plug in combination with the microfluid system according to claim 10, wherein the plug includes a closing element.

15. The plug in combination with the microfluid system according to claim 10, wherein the plug includes at least one of electronic components, liquid reservoirs, and gas reservoirs.

16. The plug in combination with the microfluid system according to claim 10, the combination configured as a single unit.

17. A plurality of plugs in combination with a respective plurality of microfluid systems, each microfluid system according to claim 10, the combinations configured as a connectable unit.

18. The plug in combination with the microfluid system according to claim 10, wherein the plug includes at least a first through-hole.

19. The plug in combination with the microfluid system according to claim 18, wherein the first through-hole is connected to a feeder.

20. The plug in combination with the microfluid system of claim 19, wherein the feeder is a flexible tube.

21. A microfluid system, comprising:
a base having at least a first flow-through channel; and
at least a first connector in fluid communication with the first flow-through channel;
wherein the base includes a surface and at least a first projection on the surface;
wherein an outer surface of the first projection is tapered from a proximate end disposed on the surface of the base to a narrower distal end elevated from the surface of the base; and
wherein the first connector includes a recess within the first projection that is tapered from a first opening at the distal end of the first projection to a narrower second opening into the first flow-through channel;
further comprising a liquid reservoir into which the first flow-through channel opens, wherein an opening of the first flow-through channel is arranged above a base surface of the liquid reservoir.

22. The microfluid system according to claim 21, wherein the liquid reservoir is arranged on a surface of the microfluid system.

23. The microfluid system according to claim 22, wherein a hollow cylinder is configured inside the liquid reservoir and extending from the base surface of the liquid reservoir, and wherein at least a section of the first flow-through channel is guided through the hollow cylinder.

24. The microfluid system according to claim 23, wherein the hollow cylinder includes a beveled surface at an opening side.

25. A microfluid system, comprising:
a base having at least a first flow-through channel; and
at least a first connector in fluid communication with the first flow-through channel;
wherein the base includes a surface and at least a first projection on the surface;
wherein an outer surface of the first projection is tapered from a proximate end disposed on the surface of the base to a narrower distal end elevated from the surface of the base; and
wherein the first connector includes a recess within the first projection that is tapered from a first opening at the distal end of the first projection to a narrower second opening into the first flow-through channel;
further comprising at least one additional flow-through channel that opens into the recess above the first flow-through channel.

* * * * *